US005739283A

United States Patent [19]
Kolattukudy et al.

[11] Patent Number: 5,739,283
[45] Date of Patent: Apr. 14, 1998

[54] PREVENTION OF INVASIVE PULMONARY ASPERGILLOSIS WITH SERINE PROTEINASE INHIBITORS

[75] Inventors: Pappachan E. Kolattukudy; Adam N. Markaryan; Edward Alan Copelan, all of Columbus; Sarah Katherine Ceselski, Delaware, all of Ohio

[73] Assignee: The Ohio State Research Foundation, Columbus, Ohio

[21] Appl. No.: 486,895

[22] Filed: Jun. 7, 1995

[51] Int. Cl.⁶ .......................... C07K 14/00; C07K 14/36
[52] U.S. Cl. .......................... 530/350; 530/412; 536/23.7
[58] Field of Search .......................... 530/330, 350, 530/412; 424/94.64; 435/219; 536/23.7

[56] References Cited

U.S. PATENT DOCUMENTS 5,166,134  11/1992  Lesday et al. .......................... 514/8

OTHER PUBLICATIONS

Obata et al. 'High-Level Expression in Streptomyces Lividans 66 of a Gene Encoding Steptomyces Subtilisin Inhibitor from Streptomyces Albogriseolus S-3253', J. Biochem., 105, pp. 372-376, 1989.

Frosco et al. Purification and Properties of the Elastase for Aspergillus fumigaus. Infection adn Immunity, vol. 60, No. 3, pp. 728-734, Mar. 1992.

Kolattukudy et al., Evidence for Possible Involvement of a Elastolytic Serine protease in Aspergillosis. Infection and Immunity, vol. 61, No. 6, pp. 2357-2368, Jun. 1993.

Ramesh et al. Isolation, Characterization, and closinign of cDNA and the Gene for an Elastinolytic Serine Proteinase from Aspergillus flavus. Infection and Immunity, vol. 62, No. 1, pp. 79-85, Jan. 1994.

Heinz et al. Changing the Inhibitory Specificity and Function of the Proteinase Inhibitor Eglin c by Site-Directed Mutagenesis: Functional and Structural Investigation. Biochemistry, vol. 31, pp. 8755-8766, 1992.

Bennett, J.E. (1990) *Aspergillus* species. In: Principles and Practice of Infectious Diseases. Mandell, G.L., Douglas, R.G., Bennett, J.E. (ed.), 3rd ed., New York, Churchill Livingstone: pp. 1958-1962.

Denning, D.W., Stevens, D.A. (1990), Antifungal and Surgical Treatment of Invasive Aspergillosis: Review of 2, 121 Published Cases. Rev. of Infectious Diseases 12 (Nov.-Dec.): 1147-1201.

Frosco, M., Chase, T. J., MacMillan, J.D. (1992) Purification and properties of the elastase from *Aspergillus fumigatus*, Infection and Immunity, 60 (Mar.):728-734.

Galloway, D.R. (1991), *Pseudomonas aeruginosa* elastase and elastolysis revisited: recent developments Molecular Microbiology 5(10): 2315-2321.

Jaton-Ogay K., Suter, M., Crameri, R., Falchetto, R., Faith A., Monod M. (1992) Nucleotide sequence of a genomic and a cDNA clone encoding an extracellular alkaline protease of *Aspergillus fumigatus*, FEMS Microbiol. Lett. 92: 163-168.

Kharazmi A. (1991) Mechanisms involved in the evasion of the host defence by *Pseudomonas aeruginosa*. Immunol. Lett. 30: 201-206.

Kolattukudy, P.E., Lee, J.D., Rogers, L.M., Zimmerman, P., Ceselski, S., Fox, B., Stein, B., Copelan, E.A. (1993) Evidence for possible involvement of an elastolytic serine protease in Aspergillosis. Infection and Immunity 61 (Jun.) 2357-2368.

Kothary, M.H., Chase, T., MacMillian J.D. (1984) Correlation of Elastase Production by Some Strains of *Aspergillus fumigatus* with Ability to Cause Pulmonary Invasive Aspergillosis in Mice, Infection and Immunity 43 (Jan.): 320-325.

Monod, M., Togni, G., Rahalison, L., Frenk, E. (1991) Isolation and Characterisation of an Extracellular Alkaline Protease of *Aspergillus fumigatus*, J. Med. Microbiol. 35: 23-38.

Monod, M., Paris, S., Sarfati, J., Jaton-Ogay, K., Ave P., Latge, J.P. (1993) Virulence of alkaline protease-deficient mutants of *Aspergillus fumigatus*, FEMS Microbiol Lett 106:39-46.

Ramesh, M.V., Sirakova, T., Kolattukudy, P.E. (1994) Isolation, Characterization, and Cloning of cDNA and the Gene for an Elastinolytic Serine Proteinase from *Aspergillus flavus*, Infection and Immunity 62 (Jan):79-85.

Reichard, U., Buttner, S., Eiffert, H., Staib, F., Ruchel, R., (1990) Purifcation and Characterization of an Extracellular Serine Proteinase from *Aspergillus fumigatus* and its Detection in Tissue, J. of Med. Microbiol. 33: 243-251.

Rhodes, J.C., Bode, R.B., McCuan-Kirsch, M. (1988) Elastase Production in Clinical Isolates of *Aspergillus*, Diagn. Microbiol. Infect. Dis 10:165-170.

Rhodes, J.C., Amlung, T.W., Miller, M.S., (1990) Isolation and Characterization of an Elastinolytic Proteinase from *Aspergillus flavus*, Infection and Immunity, 58 (Aug.):2529-2534.

(List continued on next page.)

*Primary Examiner*—Cecilia J. Tsang
*Assistant Examiner*—Anish Gupta
*Attorney, Agent, or Firm*—Calfee Halter & Griswold LLP

[57] ABSTRACT

A new, non-toxic pharmaceutical composition for the treatment and prevention of invasive pulmonary aspergillosis has been discovered. The new pharmaceutical composition includes a physiologically compatible carrier and an agent which inhibits the proteolytic activity of the extracellular elastolytic serine protease produced by aspergillus. The agent preferably comprises a serine protease inhibitor, more preferably a subtilisn-type inhibitor, most preferably streptomyces subtilisin inhibitor. Such pharmaceutical compositions are effective at reducing the incidence of mortality due to invasive pulmonary aspergillosis and are also effective at reducing the invasion of lung tissue and the tissues surrounding the lungs by the germinating hyphae of Aspergillus. The invention also relates to a method of treating invasive pulmonary aspergillosis using a pharmaceutical composition comprising a serine protease inhibitor, preferably a subtilisin-type inhibitor, more preferably a streptomyces subtilisin inhibitor and a physiologically compatible carrier.

16 Claims, 1 Drawing Sheet

OTHER PUBLICATIONS

Rinaldi, M.G. (1983) Invasive aspergillosis, Rev. Infect. Dis 5(Nov.–Dec.): 1061–1077.

Tang, C.M., Cohen, J., Krausz, T., von Noorden, S., Holden, D.W. (1993) The alkaline protease of *Aspergillus fumigatus* is not a virulence determinant in two murine models of invasive pulmonary aspergillosis. Infection and Immunity 61(May): 1650–1656.

"Changing the Inhibitory Specificity and Function of the Proteinase Inhibitor . . . " by Heinz, et al., *Biochemistry*, 1992, 31, 8755–8766.

"Structural Comparison of Two Serine Proteinase–Protein Inhibitor . . . " by McPhalen, et al., *Biochemistry* 1988, 27, 6582–6598.

PREVENTION OF INVASIVE PULMONARY ASPERGILLOSIS WITH SERINE PROTEINASE INHIBITORS

BACKGROUND OF THE INVENTION

In the past 20 years, the incidence of fungal infections has increased greatly due, in large part, to the increased number of individuals who are immunocompromised by chemotherapy, radiation therapy, or immunosuppressive drug treatments. Invasive pulmonary aspergillosis is one of the most significant fungal infections which occurs in such immunocompromised individuals. The incidence of aspergillosis in immunocompromised individuals is second only to the incidence of Candidia infections. In addition, invasive pulmonary aspergillosis is a highly lethal disease.

The first step in the pathogenesis of invasive pulmonary aspergillosis is inhalation of the airborne aspergillus spores into the small airways and alveolar spaces of the lungs. The disease does not develop beyond this stage in individuals with a competent immune system, because the macrophages present in these individuals phagocytize the spores. In contrast, the spores rapidly colonize the lungs of immunocompromised individuals who have reduced numbers of macrophages and neutrophils. As the infection progresses, the germinating hyphae invade the lung tissue and necrosis of the lungs occurs. At this point the hyphae begin to invade the tissues surrounding the lungs. When the infection reaches this stage, death usually occurs.

Unfortunately, the few anti-mycotic agents currently available to treat this fungal disease are relatively ineffective against the aspergillus pathogen. At present, amphotericin B is the most effective and most commonly used anti-mycotic agent for treating invasive pulmonary aspergillosis. Amphotericin B most likely acts by preventing one of the metabolic steps of aspergillus cell wall biosynthesis, thus preventing further colonization of the lungs and spread of the infection. However, even when amphotericin B is administered, mortality in the range of 50 to 90% is common in those immunocompromised individuals infected with Aspergillus. In addition, nephrotoxicity remains a serious side effect with amphotericin B. Accordingly, there is a great need for new, nontoxic pharmaceutical compositions which are effective at retarding the pathogenesis of invasive pulmonary aspergillosis. It is also important that these compositions do not adversely affect normal lung function.

SUMMARY OF THE INVENTION

A new, non-toxic pharmaceutical composition for the treatment and prevention of invasive pulmonary aspergillosis has been discovered. The new pharmaceutical composition includes a physiologically compatible carrier and an agent which inhibits the proteolytic activity of the extracellular elastolytic serine proteases produced by aspergillus. The agent preferably comprises a serine protease inhibitor, more preferably a subtilisn-type inhibitor, most preferably streptomyces subtilisin inhibitor. The agent may also comprise a chymotrypsin-type inhibitor, preferably potato protease inhibitor, or mixtures of subtilisin-type and chymotrypsin-type inhibitors. Such pharmaceutical compositions are effective at reducing the incidence of mortality due to invasive pulmonary aspergillosis and are also effective at reducing the invasion of lung tissue and the tissues surrounding the lungs by the germinating hyphae of Aspergillus.

The invention also relates to a method of treating invasive pulmonary aspergillosis using a pharmaceutical composition comprising a serine protease inhibitor, preferably a subtilisin-type inhibitor, more preferably streptomyces subtilisin inhibitor, and a physiologically compatible carrier. The treatment involves localized administration of the pharmaceutical composition to the patient preferably before or soon after exposure to the aspergillus spores. Preferably the pharmaceutical composition is administered repeatedly during the time the patient is immunocompromised or neutropenic.

DETAILED DESCRIPTION OF THE INVENTION

A non-toxic pharmaceutical composition for treating and preventing invasive pulmonary aspergillosis has been developed. The pharmaceutical composition contains a physiologically compatible carrier and a therapeutically effective amount of an agent which inhibits the proteolytic activity of the extracellular elastolytic serine proteases produced by aspergillus. Preferably the agent is a subtilisin-type inhibitor, more preferably streptomyces subtilisin inhibitor. The agent may also be a chymotrypsin-type inhibitor, preferably potato protease inhibitor, or mixtures of a subtilisin-type inhibitor and chymotrypsin-type inhibitor. The carrier is a pharmacologically acceptable solution, preferably a neutral isotonic buffered saline solution such as phosphate buffered saline. Preferably, the pharmaceutical composition is administered before or soon after the patient is exposed to the airborne aspergillus spores. The pharmaceutical composition is preferably administered repeatedly at intervals during the time the patient is immunocompromised or neutropenic. The composition is administered preferably by inhalation in the form of a nasal spray or nasal drops.

Administration of the pharmaceutical composition containing an inhibitor of aspergillus elastolytic serine protease reduces the incidence of mortality in immunocompromised hosts whose lungs are infected with aspergillus. This treatment also retards invasion of the lung tissue and surrounding organs in the host by aspergillus hyphae. This treatment which involves localized administration of the pharmaceutical composition to the lungs also has the advantage of not being a systemic treatment with the concomitant problems normally associated with a systemic treatment.

A method for producing substantial amounts of a recombinant form of streptomyces subtilisin protease inhibitor in yeast has also been discovered. A recombinant method which incorporates the bacterial gene for streptomyces subtilisin inhibitor into a yeast vector for expression in a yeast host produces large amounts of the biologically-pure protease inhibitor, streptomyces subtilisin inhibitor.

Isolation of Streptomyces Subtilisin Inhibitor

Streptomyces subtilisin inhibitor (SSI) is a protein produced and secreted by the bacterium streptomyces. SSI inhibits the proteolytic activity of the extracellular serine protease produced by the bacterium *Bacillus subtilis*. The inhibition of *B. subtilis* serine protease by SSI is reversible.

SSI was purified from four Streptomyces albogriseolus strains obtained from the American Type Culture Collection (ATCC), Rockville, Md. The ATCC strains were 31422, 31423, 43906 and 23875. Strains 31422, 31423, 43096, and 23875 were deposited with the American Type Culture Collection 12301 Parklawn Drive, Rockville, Md. 20852, on Nov. 26, 1996 and were assigned Accession Numbers 55889, 55890, 55891, and 55888, respectively. To confirm production of SSI by *Streptomyces albogriseolus*, each strain was first cultivated in 5 ml of a medium consisting of 4% polypeptone from Becton Dickinson Microbiology Systems, Cockeysville, Md., 2% soluble starch from Difco Laboratories, Detroit, Mich., 0.1% NaCl, 0.1% $K_2HPO_4$, 0.1% $MgSO_4 \cdot 7H_2O$; pH 7.0 (SSI medium). After cultivation at 28° C. for 5 days, the bacterial cells were separated from the culture supernatant by vacuum filtration through Whatman filter paper. The recovered supernatant was precipitated with 3 volumes of isopropanol. The resulting precipitate was dried with acetone and dissolved in 0.25 ml 20 mM Tris-HCl, pH 7.2.

To assay for the presence of subtilisin inhibitory activity in the precipitate, varying amounts of the dissolved precipitate were mixed with 1 µg of subtilisin A obtained from Calbiochem, San Diego, Calif., in a total volume of 50 µl of 20 mM Tris-HCl, pH 7.2. The samples were kept for 15 minutes at room temperature. Then 500 µl of 0.1M Tris-Cl, pH 8.0, and 100 µl of dimethylsulfoxide containing 1 mM Z-Ala-Ala-Leu-p nitroanilide (pNa) obtained from Calbiochem were added. Subtilisin A hydrolyzes the Leu-pNa bond of the chromogenic substrate and releases pNa into the solution, causing an increase in absorbance at 410 nm.

To characterize the proteins in the precipitate, a 10 µl aliquot of the dissolved precipitate was mixed with 10 µm of SDS buffer and electrophoresed for approximately 5 hours on an 18% polyacrylamide SDS denaturing gel at 100V.

The crude preparations from the four streptomyces strains inhibited the proteolytic activity of subtilisin A to comparable levels. In addition, each of the four strains contained a major protein band of about 12 kDa.

To scale up the production of SSI, the cells from each of the strains were then inoculated into 100 ml of SSI medium in 500 ml flasks and cultivated with shaking at 30° C. for 5 days. At the end of the 5 days, the cultures were vacuum filtered through Whatman filter paper and the supernatant recovered. Proteins, including SSI, were precipitated from the culture supernatant by addition of 3 volumes of isopropanol and by centrifugation at 10,000 g for 20 minutes. Each precipitate was dissolved in 2 ml of 20 mM Tris-Cl, pH 7.2 and dialyzed overnight against 1,000 ml of the same buffer. Each 2 ml solution was then applied on a Mono Q column (0.5×5 cm), washed with 20 ml of the same buffer and eluted at 1 ml/minute with a linear gradient of a 0.0–1.0M NaCl in the same buffer. One ml fractions of eluant were collected and aliquots of the fractions assayed for inhibitory activity toward subtilisin A as described above.

Most of the inhibitory activity was observed in the fractions that were eluted at 0.15M NaCl. For each strain, the eluted fractions with the highest inhibitory activity toward subtilisin A were pooled and stored at −20° C.

Figure 1:
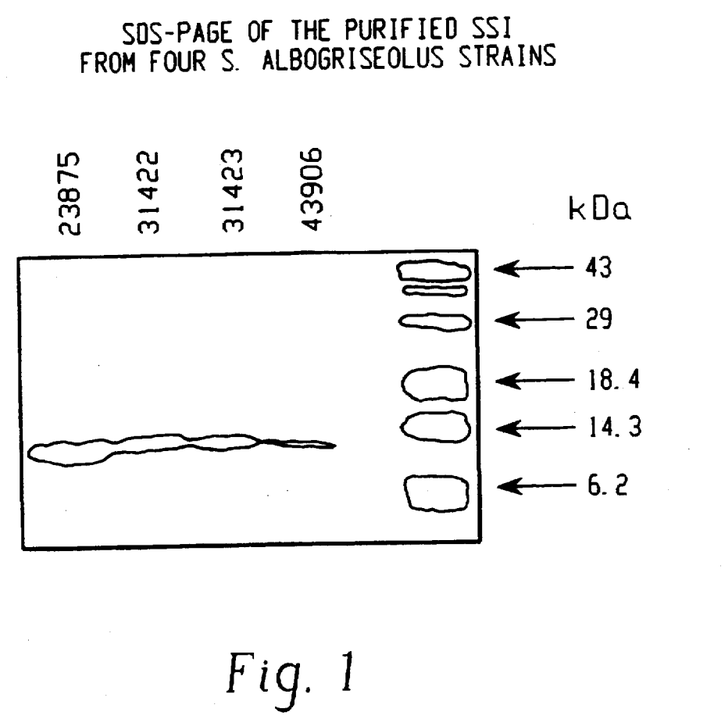
FIG. 1 is a picture of the Coomassie-Blue stained SDS gel of purified Steptomyces Subtilisin Inhibitor (SSI) isolated from four strains of *Streptomyces albogriseolus*.

The amount of protein recovered in the pooled fractions for each of the four strains was determined by the Bradford method as published in Anal. Biochem. 72: 248–254 (1976). In addition, a 10 µm aliquot of the pooled fractions for each strain were subjected to SDS-PAGE. As shown in FIG. 1, which depicts the Coomassie-Blue stained gel, the major protein purified from the culture medium of each of the four strains migrated on an SDS gel with an apparent molecular weight of 12 kDa. This SSI was used in the pharmaceutical compositions of examples 1, 2, and 3.

Preparation of Recombinant Streptomyces Subtilisin Inhibitor

Genomic DNA from *Streptomyces albogriseolus* strain 23875 strain was prepared according to the method of Hunter, I. S., "Genecloning in Streptomyces" in *DNA Cloning: A Practical Approach*, ed. D. M. Glover, pp. 19–44 (1985). In brief, the streptomyces cells harvested by vacuum filtration from 500 ml of culture fluid were resuspended in 10 ml of 10 mM Tris-HCl, 1 mM EDTA (TE), pH 8.0, and incubated for 15 minutes at 30° C. with 10 mg lysozyme to digest the cell wall. Then 1 ml of 20% SDS was added to the solution with gentle stirring. After about 15 seconds, 10 ml TE-saturated phenol and 1.5 ml 5M NaCl was added to the solution and the tube containing the solution inverted repeatedly and gently at room temperature for 20 minutes. The mixture was transferred to a 50 ml tube and centrifuged at 1500 r.p.m. for 10 minutes to separate the phases. The viscous top layer was removed with a pipette and transferred to a clean tube where it was similarly extracted two times with an equal volume of chloroform.

After the second chloroform extraction, the viscous top layer was transferred into a 100 ml beaker where the DNA was precipitated by the addition of an equal volume of isopropanol. The precipitated DNA recovered by centrifugation at 10,000×g for 10 minutes was redissolved in the minimum volume of TE. RNase A, from Sigma, St. Louis, Mo., was added to the DNA solution to a final concentration of 20 µg/ml and the solution incubated at 50° C. for 1 hour. Then protease K, from Sigma, freshly dissolved in TE was added to a final concentration of 100 µg/ml. NaCl and SDS, to final concentrations of 100 mM and 0.4%, respectively, were added to the solution. After a 1 hour incubation at 37° C., the solution was extracted with TE-phenol and chloroform as described above. The final concentration and purity of the DNA in the solution was determined by scanning absorbance from 230 to 280 nm.

Genomic DNA purified as described above was used as a template to amplify the DNA sequence encoding pre-SSI, that is, the region of DNA coding for both the signal amino acid sequence, which is cleaved by the signal peptidase during intracellular processing of the protein, and the amino acid sequence of the mature form of the protein, which is secreted by the host cells into the culture medium.

Two synthetic nucleotides were obtained from Integrated DNA, Technologies, Inc., Coralville, Iowa for use as primers. The sequence of the sense primer was 5'-ATG CGGAAC ACC GGC GCT-3'; and the sequence of the antisense primer was 5'-CCC GGT CTC TAG AAG GCG-3'. The coding sequence was amplified in a PTC-100™, MJ Research Inc., Watertown, Mass.

Amplification of the gene by polymerase chain reaction was carried out in a total volume of 50 µm containing 10 ng of genomic DNA as the template, 25 pmol of each oligonucleotide primer, 0.2 mM of each deoxynucleoside triphosphate, 20 mM Tris-HCl, pH 8.4, 50 mM KCl, 0.5 mM $MgCl_2$, 5% dimethylsulfoxide and 2U Taq polymerase from GIBCO-BRL, Gaithersburg, Md. The amplification protocol consisted of a denaturation at 94° C. followed by 30 cycles of the following steps: denaturation at 94° C. for 1 minute, annealing at 60° C. for 2 minutes and extension at 72° C. for 3 minutes. The resulting 443 bp amplification product was subcloned into pCR™II vector from Invitrogen, San Diego, Calif. according to the instructions of the manufacturer. The plasmid was then sequenced by the chain termination method of Sanger, F. et al., "DNA Sequencing with Chain Terminating Inhibitors," Proc. Nat. Acad. Sci. USA 74: 5463–5467 (1977). The sequence of the 443 bp product is listed as SEQ. ID NO. 1.

For expression of the gene encoding SSI in the yeast *Pichia pastoris*, the pre-SSI DNA cloned into pCR™II was modified by polymerase chain amplification to remove the pre-region and to introduce two restriction enzyme sites for sub-cloning into the pHIL-SI expression vector. Both primers were obtained from Integrated DNA Technologies, Inc. and comprised 24-mers. The sequence of the sense primer was 5'-GAA TTC GCC CCG GGA GAT GCC CCG-3'; the sequence of the antisense primer was 5' GGA TCC CTA GAA GGC GAA GAC GCT 3'.

Amplification of the modified gene by polymerase chain reaction was carried out in a total volume of 50 μm containing 50 ng of pCR™II-preSSI DNA vector, 20 pmol of each oligonucleotide primer, 0.2 mM of each deoxynucleoside triphosphate, 20 mM Tris-HCl, pH 8.4, 50 mM KCl, 1.5 mM $MgCl_2$, 10% dimethylsulfoxide and 2U Taq polymerase.

The amplification protocol consisted of a denaturation at 94° C. followed by 30 cycles of the following steps: denaturation at 94° C. for 45 sec, annealing at 55° C. for 30 sec and extension at 72° C. for 60 sec. The resulting 362 bp product was subcloned into pCR™ II vector.

The pCR™II-SSI was sequenced by the chain termination method of Sanger to identify clones in which the complete SSI nucleotide sequence had been inserted correctly, both as to location and orientation. The DNA sequence of the modified SSI gene is listed as SEQ. ID. NO. 2.

The modified SSI DNA fragment was excised from the pCR™II vector by co-digestion with Eco RI and Bam HI and ligated overnight at 14° into the *Pichia pastoris* expression vector pHIL-SI, which had also been co-digested with Eco. RI and Bam HI. The TA Cloning kit for expression of genes in *Pichia pastoris*, containing vector and the *Pichia pastoris* yeast strain GS 115, was obtained from Invitrogen, San Diego, Calif. The pHIL-SI expression vector contains a his4 gene as a selectable marker for identifying transformants of the yeast. The resulting vector pHIL-SI-SSI was sequenced according to the method of Sanger.

The pHIL-SI-SSI vector linearized by digestion with Bgl II from GIBCO-BRL, Gaithersburg, Md. was transformed according to the instructions from the manufacturer, Invitrogen, into competent spheroplasts of *Pichia pastoris*, also prepared according to instructions from the manufacturer. Integration of the vector at the AOX1 locus results in the complete removal of the AOX1 coding region. The resulting recombinant phenotype of the successfully transformed yeast is His+Mut–. Mut– refers to the methanol utilization minus phenotype caused by the loss of alcohol oxidase activity encoded by the AOX1 gene. Transformed yeast with the Mut– phenotype grow slowly or do not grow at all on medium containing methanol as a carbon source.

The yeast were grown on histidine-deficient media to select transformants, that is, yeast in which a recombination event between the yeast DNA and the vector DNA has occurred. Non-transformed transformed yeast are his–, that is, lack the gene for synthesizing histidine, and grow slowly on this medium. To screen for insertion of the expression vector at the correct locus within the AOX1 gene, transformants were patched, according to instructions provided by the manufacturer Invitrogen, onto two scored plates, one containing histidine deficient buffered minimal medium with 0.5% methanol as a carbon source (BMMY medium), the other containing histidine deficient buffered minimal medium with 1% glycerol as a carbon source (BMGY medium). Both media contained 1% yeast extract, 2% peptone, 0.1M phosphate buffer, pH 6.0, 0.4 mg/liter biotin and 1.34% yeast nitrogen base.

Twenty colonies having the proper phenotype, His+Mut–, were identified on the plates incubated in the BMMY medium. The corresponding colonies on the plates incubated in the glycerol-containing BMGY medium were selected and grown in 50 ml tubes containing 10 ml of BMGY media at 30° C. temp for 2 days. The cells from each of the flasks were then collected by centrifugation at 4,000×g for 10 minutes.

To induce expression of the SSI gene which, in successful transformants, is inserted behind the promoter for AOX1, a portion of the his+mut– transformants from each of the twenty colonies was resuspended in 2 ml of BMMY medium, and grown for 2 days at 30° C. with strong aeration. Each of the 20 cultures was then screened for secretion of SSI into the culture medium by assaying an aliquot of the culture medium for inhibitory activity toward Subtilisin A according to the screening procedure described above. A 30 μm aliquot of medium from each of the eleven cultures that tested positive for subtilisin inhibitory activity was also electrophoresed on a SDS-polyacrylamide gel.

All eleven clones that tested positive for subtilisn inhibitory activity secreted a protein migrating on an SDS gel with an apparent molecular weight of 12 kDa. Cells from each of these colonies were frozen.

Purification of Recombinant SSI from Pichia Pastoris Culture Fluid

A portion of the transformant expressing the most SSI protein, determined by the staining intensity of the 12 kDa band on the SDS gel, was inoculated into 30 ml of BMGY media and incubated overnight at 30° C. with vigorous shaking. The next day a 7.5 ml aliquot of the culture was inoculated into 700 ml of BMGY in a 2 liter baffled flask obtained from Nalge Company, Rochester, N.Y. The flasks were loosely capped to allow maximum aeration and the cultures were incubated for 2 days at 30° C. with vigorous shaking. After 2 days, the $OD_{600}$ in the culture flask was 16. An $OD_{600}$ between 10.0–20.0 indicates sufficient growth for harvesting the cultured cells. The cells were harvested by centrifugation at 3500 r.p.m. for 10 minutes and resuspended in 250 ml of BMMY in a 2 liter baffled flask covered with cheesecloth. Incubation of the cells at 30° C. with vigorous shaking induces expression of the cloned SSI gene. After a two day incubation, the cells were separated from the media by centrifugation at room temperature for 15 minutes and the media analyzed for secretion of the recombinant SSI protein by SDS-PAGE and by assessing the inhibitory activity of aliquots of the culture fluid toward subtilisin A as described above.

The BMMY culture fluid, which contained secreted SSI, was precipitated overnight with $(NH_4)_2SO_4$ at 80% saturation. After removal of the supernatant, the precipitate was dissolved in 15 ml of 20 mM HEPES, pH 7.2, and applied to a phenyl-sepharose column (3×27 cm) equilibrated with 2M NaCl in water. The column was washed with 200 ml of 2M NaCl in water and the bound SSI eluted with water. The active SSI fractions were combined, dialyzed overnight against water and stored at –20° C. The total yield of recombinant SSI from the 400 ml of extracellular yeast culture fluid was 200 mg.

Characterization of Naturally-Occurring and Recombinant SSI

The purified SSI isolated from strain 23875 and the recombinant SSI were first subjected to SDS-PAGE and then electroblotted to a ProBlott membrane as described by P. Matsudaira *J. Biol. Chem.* (1987), 262:10035–10038. In brief, the SDS gel was soaked in transfer buffer (10 mM 3-[cyclohexylamino]-1-propanesulfonic acid, 10% methanol, pH 11, for 5 minutes. During this time a PVDF membrane obtained from Millipore Corporation, Bedford, Mass., was rinsed with 100% methanol and stored in transfer buffer. The gel, sandwiched between a sheet of PVDF membrane and several sheets of blotting paper, was assembled into a blotting apparatus from BioRad, Hercules, Calif., and electroeluted for 40 minutes at 0.4 A in transfer buffer. The PVDF membrane was washed in water for 5 minutes, stained with 0.1% Coomassie Blue R-250 in 50% methanol for 5 minutes, and then destained in 50% methanol, 10% acetic acid for 10 minutes at room temperature. The membrane was finally rinsed in deionized $H_2O$ for 5 minutes, air dried, and stored at −20° C. The membrane region to which the 12 kDa molecular weight proteins had transferred was then cut out and directly used for N-terminal sequencing on an Applied Biosystems 475A Protein Sequencer.

A Glyco Track kit from Oxford Glyco Systems, Inc., Rosedale, N.Y., was used according to the manufacturer's instructions to determine if carbohydrate chains are present on the recombinant SSI produced in Pichia pastoris. In addition, aliquots of SSI purified from Streptomyces albogriseolus strain 23875 and the recombinant SSI were subjected to electrophoresis on a Tricine 16% polyacrylamide SDS gel at 100V for 6 hours to determine the apparent molecular weight of purified and recombinant SSI.

A comparison of the properties of recombinant SSI with purified SSI isolated from strain 23875 is shown in Table I.

TABLE 1

Comparison of the Properties of Purified SSI and Recombinant SSI:

|  | Purified SSI | Recombinant SSI |
| --- | --- | --- |
| Molecular weight | 11.5 kDa | 12.0 kDa |
| Yield | 100 mg/l | 500 mg/l |
| Glycosylation | no | no |
| N-terminal sequence | APGDAPSAL | REFAPGDAPSAL |

The recombinant SSI secreted into the medium by transformed Pichia pastoris contains three additional amino acid residues in the N-terminal region when compared to SSI isolated from strain S-23875. The nucleotides encoding the two extra amino acids, Glu and Phe, are incorporated into the SSI gene during the second amplification procedure which also adds the EcoRI and BamHI restriction sites to the mature SSI gene.

Purified SSI isolated from the culture fluid of strain 23875 exhibits an apparent molecular weight of 11.5 kDa on the SDS gel and is not glycosylated. The recombinant SSI which exhibits an apparent molecular weight of 12 kDa on the SDS gel is also not glycosylated. The higher molecular weight of the recombinant SSI is most likely due to the presence of the additional amino acids found at the N-terminus of the recombinant protein.

Preparation of Other Subtilisin-Type and Chymotrypsin-Type Serine Protease Inhibitors The bifunctional A-amylase/subtilisin inhibitor of barley (ASI), was purified from barley flour using the procedure described by R. J. Weselake, et al. in "Purification and characteristics of an endogenous a-amylase inhibitor from barley kernels," 1983, Plant Physiol. 73: 1008–1012, which is incorporated herein by reference.

The chymotrypsin-type protease inhibitor Eglin C was obtained from Calbiochem. The potato chymotrypsin-type protease inhibitors I1 and I2, were provided by Dr. C. A. Ryan, Washington State University, Pullman, Wash. Methods which can be used to isolate potato protease inhibitors I1 and I2 are described in Melville, J. and Ryan, C., "Chymotrypsin inhibitor I from potatoes. Large scale preparation and characterization of its subunit components," J.Biol. Chem. 247:3445–53 (1972); and Bryant, J. et. al., "Proteinase inhibitor I1 from potatoes: isolation and characterization of its protomer components," Biochem. 15:3418–24 (1976), which are incorporated herein by reference.

In Vitro Analysis of Elastolytic Serene Protease Inhibitors

The aspergillus organism produces a number of extracellular proteases including (1) elastinolytic serine type proteases; (2) elastinolytic metalloproteases; (3) non-elastolytic metalloproteases; (4) acid proteases; and (5) collagenases. The elastinolytic serine proteases of two species of aspergillus were isolated and used to assess the effect of subtilisin-type inhibitors, chymotrypsin-type inhibitors and other known serine protease inhibitors on the activity of aspergillus serine protease.

The extracellular serine proteases of A. fumigatus and A. flavus were purified from 5 day cultures. The extracellular fluid from each culture was separated from the fungal mat by filtration and the fluid was then applied directly onto a bacitracin-Sepharose 4B column. The bound protein was sequentially eluted first with 50 mM Tris-HCl, pH 7.2, and then with 50 mM Tris-HCl, pH 7.2, containing 1M NaCl and 7% 2-propanol. The serine proteases of aspergillus eluted with the 7% 2-propanol-containing buffer. Aliquots of the fractions containing the serine protease activity were pooled and concentrated by 2-propanol precipitation. The pellets were redissolved in 0.1M Tris-HCl, pH 7.2 and dialyzed against the same buffer. The final preparations were concentrated and stored at −20° C.

Studies with Subtilisn-Type and Chymotrypsin-Type Inhibitors

Subtilisin-type inhibitors are strong reversible inhibitors of the serine protease subtilisin, and chymotrypsin-type inhibitors are strong reversible inhibitors of the serine protease chymotrypsin. Reversible inhibitors reversibly bind to the active site of an enzyme, thereby forming a dissociable enzyme-inhibitor complex which is unable to hydrolyze proteins. Reversible inhibitors which do not rapidly dissociate from the protease-inhibitor complex, i.e., which have a low $K_i$, are considered to be stronger or better inhibitors of the protease than the reversible inhibitors which rapidly dissociate from the protease-inhibitor complex, i.e., which have a high $K_i$.

To determine whether subtilisin-type and chymotrypsin-type inhibitors are effective at reducing the proteolytic activity of the elastolytic serine proteases produced by A. fumigatus and A. flavus, the $K_i$ of several subtilisn-type inhibitors and the $K_i$ of several chymotrypsin-type inhibitors were determined.

First the $K_m$ values of the elastolytic serine proteases from A. fumigatus and A. flavus were calculated. The $K_m$ of a protease is a measure of the enzyme binding to a particular substrate and varies with pH and temperature. The $K_m$ of the elastolytic serine proteases from A. fumigatus and A. flavus were determined using the synthetic chromogenic molecule Suc-Ala-Ala-Pro-Leu-pNa as a substrate. Reaction mixtures were prepared containing 5 μm of various concentrations of the chromogenic substrate dissolved in dimethyl sulfoxide, 990 μm of 0.1M Tris-HCl, buffer pH 8.0, and 5 μm of the aspergillus protease (0.65 mg/ml). The release of pNa from the substrate and the subsequent increase in absorbance of the reaction mixture at 410 nm was monitored at 22° C. for 10 minutes using a Hewlett Packard 8451A diode array spectrophotometer. The initial rates of the enzymatic reaction at 22° C. were then determined for each concentration of substrate and the reciprocals plotted on a Lineweaver-Burk plot. The $K_m$ of *A. fumigatus* serine protease at 22° C., pH 8.0, with the substrate Suc-Ala-Ala-Pro-Leu-pNa was $3.5 \times 10^{-4}$M. The $K_m$ of *A. flavus* serine protease at 22° C., pH 8.0, with the substrate Suc-Ala-Ala-Pro-Leu-pNa was $5.7 \times 10^{-4}$M.

Next the ability of the reversible subtilisin-type inhibitors Barley ASI, purified SSI, and recombinant SSI and of the reversible chymotrypsin-type inhibitors Eglin C, potato protease I1, and potato protease I2 to block hydrolysis of the synthetic chromogenic substrate by the aspergillus elastolytic serine proteases was evaluated. Various concentrations of each inhibitor were pre-incubated for 5 minutes in samples containing the buffer and protease. Then various concentrations of the chromogenic substrate were added to the samples. The enzyme activity, or amount of pNA released from the chromogenic substrate per minute per ml of enzyme, in each sample was determined by monitoring the absorbance of the solution at 410 nm at 22° C. for 10 minutes. The enzyme activity was then used to calculate the inhibition constants, $K_i$, of the various protease inhibitors from their apparent inhibitor constants $K_i$(app) by the method of Bieth, J., (1976) "Some Kinetic Consequences of the Tight Binding of Protein-Proteinase Inhibitors to Proteolytic Enzymes and Their Application to the Determination of Association Constants," Bayer Symp. on Proteinase Inhibitors, pp. 467–69.

Inhibition constants of the reversible inhibitors for *A. fumigatus* elastolytic serine protease and *A. flavus* elastolytic serine protease are shown in Table 2

TABLE 2

Inhibition of *Aspergillus* serine protease by chymotrypsin-type and subtilisin-type serine protease inhibitors.

|  | $K_i$ for *A. fumigatus* protease | $K_i$ for *A. flavus* protease |
|---|---|---|
| Chymotrypsin-Type Inhibitors |  |  |
| Eglin C | $3.3 \times 10^{-7}$ M | N.A |
| Potato I1 | $7.4 \times 10^{-9}$ M | N.A |
| Potato I2 | $2.6 \times 10^{-8}$ M | N.A |
| Subtilisin-Type Inhibitors |  |  |
| Barley ASI | $7.7 \times 10^{-8}$ M | N.A |
| Recombinant SSI | $1.1 \times 10^{-9}$ M | $1.0 \times 10^{-8}$ M |
| SSI from S.a. 31422 | $1.9 \times 10^{-9}$ M | N.A |
| SSI from S.a. 31423 | $1.45 \times 10^{-9}$ M | N.A |
| SSI from S.a. 43906 | $6.5 \times 10^{-9}$ M | N.A |
| SSI from S.a. 23875 | $0.95 \times 10^{-9}$ M | N.A |

*N.A. - Not available

As shown in Table 2, all of the subtilisin-type and chymotrypsin-type inhibitors inhibited the elastolytic serine protease from *A. fumigatus*, with recombinant SSI and purified SSI having the greatest inhibitory effect, i.e., lowest $K_i$. The $K_i$ of potato protease I1 is comparable to the $K_i$ of SSI isolated from *S. albogriseolus* 43906 indicating that the chymotrypsin-type inhibitors isolated from potatoes are also good inhibitors of *A. fumigatus* elastolytic serine protease. As shown in Table 2, recombinant SSI is also an effective inhibitor of the elastolytic serine protease produced by *Aspergillus flavus*. These results establish that both purified SSI and recombinant SSI are very strong inhibitors of aspergillus elastolytic serine proteases.

Comparative Studies Using Other Serine Protease Inhibitors

The serine protease inhibitors 4-carboxamido-substituted cephem (L-658,758), (S-(R*,S*))-4-((3,3-diethyl-1-((1-(4-methyl-phenyl)butylamino)carbonyl)-4-oxo-2-azetidinyl)oxy)-benzeneacetic acid 2-amino-2-methyl-1-propanol salt (L-680, 833) are known to irreversibly bind to the active site of the elastolytic serine protease obtained from neutrophils. It is also known that the serine protease inhibitor PMSF irreversibly binds to the active site of all serine proteases. The ability of the serine protease inhibitors L-658,758 and L-680,833, both of which were obtained from Merck Chemical Company, Rahway, N.J., and PMSF to block the proteolytic activity of the elastolytic serine proteases from *Aspergillus fumigatus* and *Aspergillus flavus* were tested as follows.

Reaction mixtures for each protease were prepared by adding the protease to 0.1M Hepes, pH 7.5. The experimental samples were then preincubated for 30 minutes at 22° C. with 1 mM of the inhibitors. At the end of the 30 minute pre-incubation, the chromogenic substrate Suc-Ala-Ala-Pro-Leu-p-Na at a final concentration of 1 mM was added to each sample. The enzyme activity in the samples was monitored by measuring the release of pNA from the chromogenic substrate at 22° C. during a 10 minute reaction time. The enzyme activity in each experimental sample as a percentage of the enzyme activity in the control sample which was taken to be 100% was then determined.

A comparison of the activities of the Aspergillus serine proteases and a mammalian serine protease in the presence and absence of the serine protease inhibitors L-658,758, L-680,833 and PMSF is shown in Table 3.

TABLE 3

Comparison of the inhibitory effects of the serine protease inhibitors L-658,758, L-680,833, and PMSF on aspergillus serine proteases and porcine pancreatic elastolytic serine protease.

| | | | Serine protease (SP) activity (%) | | |
|---|---|---|---|---|---|
| Inhibitor | Conc (mM) | pH | *A. fumigatus* Serine Protease | *A. flavus* Serine Protease | Porcine pancreas Serine Protease |
| None | — | 7.5 | 100 | 100 | 100 |
| L658,758 | 1 | 7.5 | 93 | 91 | 6.6 |
| L680,833 | 1 | 7.5 | 93 | 89 | 12 |
| PMSF | 1 | 7.5 | 0.89 | 0 | 0 |

658,758 - 4-carboxamido-substituted cephem
680,833 - (S-(R*,S*))-4-((3,3-diethyl-1-((1-(4-methyl-phenyl)butylamino)carbonyl)-4-oxo-2-azetidinyl)oxy)-benzeneacetic acid 2-amino-2-methyl-1-propanol salt As shown in Table 3, the serine protease inhibitors L-658,758 and L-680,833 are ineffective at preventing the hydrolysis of Suc-Ala-Ala-Pro-Leu-pNA substrate by the extracellular elastolytic serine proteases from *A. fumigatus* or *A. flavus*. These two inhibitors were, however, effective at reducing the activity of porcine serine protease. PMSF reduced the enzymatic activity of the two serine proteases from aspergillus and porcine serine protease.

These in vitro experiments establish that only certain serine protease inhibitors are effective at inhibiting the proteolytic activity of aspergillus elastolytic serine proteases. The serine protease inhibitors L-658,758 and L-680, 833, which are known to inhibit other elastolytic serine proteases, are ineffective at reducing the proteolytic activity of aspergillus elastolytic serine proteases.

The serine protease inhibitor PMSF effectively blocks the catalytic activity of the aspergillus elastolytic serine proteases. However, PMSF is highly toxic.

Preparation of Pharmaceutical Compositions

The phamaceutical compositions are prepared by adding a therapeutically effective amount of either a subtilisin-type inhibitor or a chymotrypsin-type inhibitor or mixtures thereof to an inert physiologically compatible carrier. Preferably the inhibitors have a $K_i$ of about $2.0 \times 10^{-8}$M or less for aspergillus serine proteases using the chromogenic substrate Suc-Ala-Ala-Pro-Leu-pNa at 22° C. and pH 8.0. More preferred are subtilisin-type inhibitors having a $K_i$ of about $1 \times 10^{-8}$M or less, and most preferred are subtilisin type inhibitors having a $K_i$ of of about $1 \times 10^{-8}$M to about $1 \times 10^{-11}$M. Thus, subtilisin-type inhibitors having a $K_i$ of about $7.0 \times 10^{-9}$M to about $1.0 \times 10^{-11}$M for the serine protease of *Aspergillus fumigatus* are among the most preferred inhibitors to use in the pharmaceutical composition. The carriers include for example a neutral buffered saline, preferably phosphate buffered saline, a saline solution, a dilute buffer, and distilled water.

EXAMPLE 1

The pharmaceutical composition was prepared by adding purified SSI isolated from strain 23875 to phosphate-buffered saline, pH 7.4, at a concentration of 50 mg/ml.

EXAMPLE 2

The pharmaceutical composition was prepared by adding purified SSI isolated from strain 23875 to phosphate-buffered saline, pH 7.4, at a concentration of 25 mg/ml.

EXAMPLE 3

To prepare the pharmaceutical composition, SSI isolated from strain 23875 was dialyzed 2x against 2 liters $dH_2O$ overnight to remove any residual salt and then added to phosphate-buffered saline, pH 7.4, at a concentration of 25 mg/ml.

EXAMPLE 4

The pharmaceutical composition was made by adding potato protease inhibitor PI2 to PBS, pH 7.4, at a concentration of 10 mg/ml.

In Vivo Evaluation of the Pharmaceutical Compositions

Tests were conducted to assess the effect of treatment with the pharmaceutical compositions of the present invention on the pathogenesis of invasive pulmonary aspergillosis in immunocompromised animals. To prevent secondary bacterial or viral infections in the treated and control animals, pathogen-free eight-week old female Balb/c mice were housed in a Bioclean laminar flow hood and provided with oxytetracylcine (100 mg/l)-neomycin sulfate (10 mg/l), pH 2.5, from 7 days prior to irradiation until the end of each experiment. Following seven days of treatment with the antibiotics, one group of animals was made immunodeficient by exposure to 400 rads of gamma radiation from a Cesium 137 source. The irradiated animals exhibited neutropenia, i.e., negligible levels of leukocytes and polymorphonuclear cells in the blood, by four days after irradiation.

Experiment 1

On the fourth day following irradiation, one group of irradiated mice and one group of control, non-irradiated mice were inoculated intra-nasally first with $5 \times 10^8$ *A. fumigatus* spores suspended in 20 µm of 0.1% Tween and then with 10 µm of Tween alone. This results in the delivery of approximately $5 \times 10^7$ *A. fumigatus* spores to the lungs of the aspergillus-inoculated mice.

Each of fourteen irradiated mice that had been inoculated with the spores received 10 µm of the pharmaceutical composition of example 1 at 10 minutes after inoculation. Over the next 48 hours each treated animal received an additional 10 µm drop of the pharmaceutical composition at 8 hour intervals for a total of seven treatments with a total of 3.5 mg of SSI.

To test the toxicity of the pharmaceutical composition of example 1, a second group of irradiated mice, inoculated with 30 ul of Tween alone were treated with a 10 µm drop the pharmaceutical composition from example 1 according to the same schedule for a total of seven treatments.

Another group of fourteen irradiated, aspergillus-inoculated animals received 10 µl PBS at 10 minutes after inoculation and at 8 hour intervals thereafter to form a group of untreated animals. The survival rates of the treated and untreated animals are shown in Table 4.

TABLE 4

Survival Rates of Mice Treated with SSI of the Pharmaceutical Composition of Example 1.

| Time After Inoculation with $5 \times 10^8$ Spores (HOURS) | Deaths in Untreated Group of Animals | Deaths in Treated Group of Animals |
| --- | --- | --- |
| 24 Hours | 0 | 0 |
| 32 Hours | 3 | 2 |
| 40 Hours | 4 | 0 |
| 48 Hours | 0 | 0 |
| Total | 7 | 2 |
| Deaths | Out of 14 Animals | Out of 14 Animals |

Fifty percent of the untreated, irradiated, aspergillus-inoculated mice died within forty-eight hours after inoculation. These animals were autopsied and their lungs stained and examined for evidence of aspergillosis. In all of these animals the lungs were grossly softened and highly invaded with *A. fumigatus* hyphae. The hyphae had also penetrated into the surrounding tissue including the intestinal wall. There was no evidence of trauma or bacterial or viral infections in these animals, indicating that aspergillosis was the cause of death. In contrast, only 15% of the animals treated with the pharmaceutical composition of example 1 died within 48 hours after inoculation with *A. fumigatus*. Thus, the composition of example 1, which contains SSI, reduces the incidence of mortality in immunocompromised animals infected with aspergillus by about 70%.

Nonirradiated controls inoculated with *A. fumigatus* spores showed no mortality, indicating that animals with a competent immune system are resistant to the pathological effects of aspergillus. Immunocompromised, neutropenic mice that received no fungal spores showed no mortality. In addition, the treated, uninoculated, immunocompromised animals showed no mortality, establishing that SSI is non-toxic.

Experiment 2

On the fourth day following irradiation all of the mice were inoculated intra-nasally first with $5 \times 10^8$ *A. fumigatus* spores suspended in 20 µm of 0.1% Tween and then with 10 µm of Tween alone. To test the efficacy of treatment with a pharmaceutical composition having a lower concentration of SSI, fourteen of the irradiated, aspergillus-inoculated animals were treated with 10 µm of the pharmaceutical composition of example 2 at 10 minutes after inoculation and at 8 hour intervals thereafter over a 48 hour period. Thus, the total amount of SSI administered to each animal over 48 hours was reduced from 3.5 to 1.75 mg.

Fourteen irradiated animals that had been inoculated with aspergillus received 10 ul drops of PBS according to the same schedule to form a group of untreated animals. The survival of the treated animals as compared to untreated animals is shown below in Table 5.

TABLE 5

Survival Rates of Mice Treated with SSI of the Pharmaceutical Composition of Example 2.

| Time After Inoculation with $5 \times 10^8$ Spores (HOURS) | Deaths in Untreated Group of Animals | Deaths in Treated Group of Animals |
| --- | --- | --- |
| 24 Hours | 0 | 0 |
| 32 Hours | 2 | 0 |
| 40 Hours | 0 | 0 |
| 48 Hours | 1 | 0 |
| 56 Hours | 0 | 1 |
| 30 Days | N.A | 0 |
| Total Deaths | 4 Out of 14 Animals | 1 Out of 14 Animals |

*N.A - Not available

Approximately 30% of the untreated, immunocompromised animals died within 48 hours after inoculation with $5 \times 10^8$ A. fumigatus spores. In contrast, over 90% of the immunocompromised animals treated with the pharmaceutical composition of example 2 survived inoculation with the aspergillus spores.

In this experiment the treated animals were maintained for an additional month. During this period none of the treated animals died or exhibited any residual side effects to treatment with the pharmaceutical composition of example 2.

Experiment 3

On the fourth day following irradiation all of the mice were inoculated intra-nasally first with $5 \times 10^8$ A. fumigatus spores suspended in 20 µm of 0.1% Tween and then with 10 µm of Tween alone. One group of mice received seven treatments with 10 µm of the pharmaceutical composition of example 3 at 8 hour intervals over a 48 hour period commencing at 10 minutes after inoculation with the spores. The concentration of purified SSI in each 10 µm treatment was 250 µg.

A second group of mice received 10 µm of PBS alone according to the same schedule. The effect of treatment with the pharmaceutical composition of example 3 on the survival of aspergillus-inoculated immunocompromised animals is shown in Table 6.

TABLE 6

Survival Rates of Mice Treated with SSI of the Pharmaceutical Composition of Example 3.

| Time After Inoculation with $5 \times 10^8$ Spores (HOURS) | Deaths in Untreated Group of Animals | Deaths in Treated Group of Animals |
| --- | --- | --- |
| 24 Hours | 0 | 0 |
| 32 Hours | 2 | 0 |
| 40 Hours | 3 | 0 |

TABLE 6-continued

Survival Rates of Mice Treated with SSI of the Pharmaceutical Composition of Example 3.

| Time After Inoculation with $5 \times 10^8$ Spores (HOURS) | Deaths in Untreated Group of Animals | Deaths in Treated Group of Animals |
| --- | --- | --- |
| 48 Hours | 3 | 2 |
| Total Deaths | 8 Out of 17 Animals | 2 Out of 14 Animals |

Almost 50% of the untreated animals died during the first 48 hours after inoculation with aspergillus, whereas only 12% of the treated animals died during this period. Thus, treatment with the SSI of pharmaceutical composition of example 3 significantly increases the survival rate of immunocompromised animals infected with aspergillus.

Three treated and three untreated surviving animals were sacrificed at 72 hours after inoculation with aspergillus and their lungs examined. The lungs of the untreated animals were grossly softened and showed signs of necrosis. In contrast, the lungs of the neutropenic mice receiving spores and a total dose of 1.75 mg of SSI had a firmer consistency. These results demonstrate that treatment with SSI of the pharmaceutical composition of example 3 retards the invasion of the lungs by A. fumigatus hyphae.

Experiment 4

On the fourth day following irradiation, the irradiated mice in one group were inoculated intra-nasally first with $1 \times 10^8$ A. fumigatus spores suspended in 20 µm of. 0.1% Tween and then with 10 µm of Tween alone. This results in the delivery of approximately $1 \times 10^7$ A. fumigatus spores to the lungs of the aspergillus-inoculated mice.

To maintain the neutropenia of the irradiated animals during this experiment, the animals were injected subcutaneously with 2 mg of cortisone acetate in 0.1% Tween every two days beginning at 8 to 12 hours after inoculation with the fungal spores.

Twenty-five of the irradiated, aspergillus-inoculated animals received 10 µm of the pharmaceutical composition of example 4, which contains 100 ug of potato protease inhibitor I2, at 10 minutes after inoculation and at 8 hour intervals thereafter for the next 72 hours. The total amount of potato protease inhibitor administered to each treated animal was 1.0 mg. Twenty-five, untreated, irradiated animals received 10 µm of PBS alone according to the same schedule.

Twenty-five, irradiated, uninoculated animals were also treated with 10 µm of the pharmaceutical composition of example 4 according to the same schedule to assess the toxicity of the composition containing potato protease inhibitor in immunocompromised animals. The effect of treatment with the pharmaceutical composition of example 4 on the survival of uninoculated and aspergillus-inoculated animals is shown in Table 7.

TABLE 7

Survival Rate of Mice Treated with Potato Protease Inhibitor of the Pharmaceutical Composition of Example 4.

| Time After Inoculation (Hours) | Deaths in Untreated Inoculated Group | Deaths in Treated Inoculated Group | Deaths in Treated Uninoculated Group |
|---|---|---|---|
| 48 | 2 | 0 | 0 |
| 56 | 2 | 0 | 0 |
| 64 | 1 | 0 | 0 |
| 72 | 1 | 0 | 0 |
| Total Deaths | 6 Out of 25 Animals | 0 Out of 25 Animals | 0 Out of 25 Animals |

No deaths were observed in any group between 0 and 40 hours after inoculation

Approximately 25% of the untreated animals died during the 72 hour period after inoculation with *A. fumigatus* spores. In contrast, none of the inoculated animals receiving pharmaceutical composition of Example 4 died during this period. Thus, pharmaceutical compositions containing the chymotrypsin-type inhibitor PI2 protect against invasive pulmonary aspergillosis. The uninoculated immunocompromised mice receiving the pharmaceutical composition of Example 4 exhibited no mortality establishing the non-toxicity of this composition.

DISCUSSION

The pharmaceutical compositions of the present invention can be used to successfully treat and prevent invasive pulmonary aspergillosis. Administration of these pharmaceutical compositions significantly reduces the incidence of mortality in aspergillus-infected immunocompromised hosts. Treatment with these pharmaceutical compositions also retards invasion by fungal hyphae of the lung tissue and surrounding organs in the aspergillus-infected immunocompromised host.

Thus, the pathogenesis of invasive pulmonary aspergillosis in immunocompromised patients can be retarded by a localized, i.e,. non-systemic, treatment using the pharmaceutical compositions of the present invention. While the compositions can be administered to the lungs of the patient in the form of nasal drops, nasal sprays or oral sprays are also suitable model of administration.

Although certain embodiments of this invention have been shown and described, various adaptations and modifications can be made without departing from the scope of the appended claims.

What is claimed is:

1. A method of treating invasive pulmonary aspergillosis in a host comprising the following steps:
   (a) providing a pharmaceutical composition comprising: a carrier; and a therapeutically effective amount of a subtilisin-type serine protease inhibitor; and
   (b) administering said pharmaceutical composition to the lungs of the host.

2. The method of claim 1 wherein the pharmaceutical composition is administered nasally.

3. The method of claim 1 wherein the subtilisin-type serine protease inhibitor is encoded by a nucleic acid having the nucleotide sequence of SEQ. ID. NO. 1.

4. The method of claim 1 wherein the serine protease inhibitor is a subtilisin-type inhibitor purified from streptomyces.

5. The method of claim 1 wherein the serine protease inhibitor is a recombinant streptomyces subtilisin inhibitor.

6. The method of claim 1 wherein said serine protease inhibitor has a $K_i$ of about $2.0 \times 10^{-8}$ or less for a serine protease of Aspergillus measured at 22° C. and pH 8.0 using the chromogenic substrate Suc-Ala-Ala-Pro-Leu-pNa.

7. The method of claim 6 wherein said serine protease inhibitor is a subtilisin-type inhibitor and has a $K_i$ of about $1.0 \times 10^{-8}$ M or less.

8. The method of claim 6 wherein said serine protease inhibitor is a subtilisin-type inhibitor and has a $K_i$ of about $1.0 \times 10^{-8}$ to about $1 \times 10^{-11}$ M.

9. The method of claim 6 wherein said serine protease inhibitor is a subtilisin-type inhibitor and has a $K_i$ of about $7 \times 10^{-9}$ M to about $1 \times 10^{-11}$ M for a serine protease of *Aspergillus fumigatus*.

10. The method of claim 1 wherein said subtilisin-type serine protease inhibitor is encoded by a nucleic acid comprising the nucleotide sequence of SEQ. ID. NO. 2.

11. The method of claim 1 wherein said serine protease inhibitor is purified from *Streptomyces albogriseolus* strain 23875.

12. The method of claim 1 wherein said serine protease inhibitor is purified from *Streptomyces albogriseolus* strain 31422.

13. The method of claim 1 wherein said serine protease inhibitor is purified from *Streptomyces albogriseolus* strain 31423.

14. The method of claim 1 wherein said serine protease inhibitor is purified from *Streptomyces albogriseolus* strain 43906.

15. The method of claim 1 wherein the host is neutropenic.

16. The method of claim 1 wherein said pharmaceutical composition is administered nasally to the host at least two times during the neutropenic period; and said carrier comprises phosphate-buffered saline.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 443 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: YES     ( i v ) ANTI-SENSE: NO     ( x i ) SEQUENCE DESCRIPTION: SEQ ID NO:1:

```
ATGCGGAACA  CCGGCGCTGG  GCCATCACCC  TCGGTCTCAC  GGCCACCGCC  GTCTGCGGCC      60
CCCCTCTCCG  GGGCCGCGCT  CGCCGCCCCG  GGAGATGCCC  CGTCCGCGCT  CTACGCCCCC     120
TCCGCCCTGG  TGCTGACCGT  CGGCAAGGGC  GTCAGCGCGA  CGACCGCCGC  ACCGGAACGC     180
GCGGTCACCC  TGACCTGTGC  TCCGGGCCCG  TCGGGCACCC  ACCCGGCGGC  CGGCTCGGCC     240
TGCGCGGACC  TGGCCGCCGT  CGGCGGCGAC  CTGAACGCGC  TGACGCGGGG  CGAGGACGTC     300
ATGTGCCCGA  TGGTGTACGA  CCCGGTGCTG  CTCACCGTGG  ACGGCGTCTG  GCAGGGCAAG     360
CGGGTCTCCT  ACGAGCGCGT  CTTCTCCAAC  GAGTGCGAGA  TGAACGCGCA  CGGCTCGAGC     420
GTCTTCGCCT  TCTAGAGACC  GGG                                               443
```

( 2 ) INFORMATION FOR SEQ ID NO:2:

( i ) SEQUENCE CHARACTERISTICS:
        ( A ) LENGTH: 362 base pairs
        ( B ) TYPE: nucleic acid (C) STRANDEDNESS: double
(D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO:2:

```
GAATTCGCCC CGGGAGATGC CCCGTCCGCG CTCTACGCCC CCTCCGCCCT GGTGCTGACC        60
GTCGGCAAGG GCGTCAGCGC GACGACCGCC GCACCGGAAC GCGCGGTCAC CCTGACCTGT       120
GCTCCGGGCC CGTCGGGCAC CCACCCGGCG GCCGGCTCGG CCTGCGCGGA CCTGGCCGCC       180
GTCGGCGGCG ACCTGAACGC GCTGACGCGG GGCGAGGACG TCATGTGCCC GATGGTGTAC       240
GACCCGGTGC TGCTCACCGT GGACGGCGTC TGGCAGGGCA AGCGGGTCTC CTACGAGCGC       300
GTCTTCTCCA ACGAGTGCGA GATGAACGCG CACGGCTCGA GCGTCTTCGC CTTCTAGGAT       360
CC                                                                     362
```